United States Patent [19]
Epstein et al.

[11] Patent Number: 5,997,883
[45] Date of Patent: Dec. 7, 1999

[54] RETROSPECTIVE ORDERING OF SEGMENTED MRI CARDIAC DATA USING CARDIAC PHASE

[75] Inventors: Frederick H. Epstein, Gaithersburg; Andrew E. Arai, Kensington, both of Md.; Jeffrey A. Feinstein, Alexandria, Va.; Thomas K. Foo, Rockville; Steven D. Wolff, Bethesda, both of Md.

[73] Assignee: General Electric Company, Milwaukee, Wis.

[21] Appl. No.: 08/886,487

[22] Filed: Jul. 1, 1997

Related U.S. Application Data
[60] Provisional application No. 60/043,535, Apr. 11, 1997.

[51] Int. Cl.$^6$ ....................................... G01V 3/00
[52] U.S. Cl. ........................... 424/306; 324/309; 324/307; 324/306; 324/322; 600/439; 600/413; 600/424
[58] Field of Search ..................................... 324/309, 307, 324/306, 329; 600/439, 413, 424

[56] References Cited

U.S. PATENT DOCUMENTS
| | | | |
|---|---|---|---|
| 4,710,717 | 12/1987 | Pelc et al. ................................. | 324/309 |
| 5,377,680 | 1/1995 | Bernstein et al. .................... | 128/653.2 |

OTHER PUBLICATIONS

Improved Ejection Fraction and Flow Velocity Estimates with Use of View Sharing and Uniform Repetition Time Excitation with Fast Cardiac Techniques, Radiology 1995; 195:471–478, Foo, et al.

Techniques to Improve the Accuracy of Coronary Flow Measurements, Dept. Of Medical Physics & Radiology, Univ. Of WI, Madison, p. 602, Polzin, et al.

Relations of the Systolic Time Intervals to Heart Rate, Mirsky I., Cardiac Mechanics: Physiological, Clinical and Mathematical Consideration, John Wiley & Sons, Inc. New York 1974, pp. 237–241.

MR Imaging Characterization of Postischemic Myocardial Dysfunction ("Stunned Myocardium"): Relationship Between Functional and Perfusion Abnormalities, JMRI, 1996; 6:615–624, Szolar, et al.

Comparison of Fixed and Variable Temporal Resolution Methods for Creating Gated Cardiac Blood–Pool Image Sequences, Journal of Nuclear Medicine, vol. 31, No. 1, pp. 38–42, Jan. 1990, Bacharach, et al.

Evaluation of Left Ventricular Volume and Mass with Breath–hold Cine MR Imaging, Radiology 1993; 188:377–380, Sakuma, et al.

*Primary Examiner*—John Barlow
*Assistant Examiner*—Brij B. Shrivastav
*Attorney, Agent, or Firm*—Quarles & Brady; Christian G. Cabou; Phyllis Y. Price

[57] ABSTRACT

A method is disclosed to reconstruct multiphase MR images that accurately depict the entire cardiac cycle. A segmented, gradient-recalled-echo sequence is modified to acquire data continuously. Images are retrospectively reconstructed by selecting views from each heartbeat based on cardiac phase rather than the time elapsed from the QRS complex. Cardiac phase is calculated using a model that compensates for beat-to-beat heart rate changes.

8 Claims, 4 Drawing Sheets

RETROSPECTIVE ORDERING OF SEGMENTED MRI CARDIAC DATA USING CARDIAC PHASE

RELATED APPLICATION

This application is based on Provisional Application No. 60/043,535 filed on Apr. 11, 1997.

BACKGROUND OF THE INVENTION

The field of the invention is nuclear magnetic resonance imaging methods and systems. More particularly, the invention relates to the production of images in a fast cardiac MRI acquisition.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$ $G_y$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Most NMR scans currently used to produce medical images require many minutes to acquire the necessary data. The reduction of this scan time is an important consideration, since reduced scan time increases patient throughput, improves patient comfort, and improves image quality by reducing motion artifacts. There is a class of pulse sequences which have a very short repetition time (TR) and result in complete scans which can be conducted in seconds rather than minutes. When applied to cardiac imaging, for example, a complete scan from which a series of images showing the heart at different phases of its cycle or at different slice locations can be acquired in a single breath-hold.

There are two common techniques for acquiring cardiac MR images. The first is a prospectively gated, single-phase, multi-slice conventional spin echo sequence. In each cardiac cycle, data at different spatial locations are acquired with the same k-space phase encoding value. Images at the different spatial locations are then acquired at different temporal phase of the cardiac cycle. Since only one k-space line is acquired per cardiac trigger, a typical scan with a 128 k-space views in the phase encoding direction will take 128 heart beats to complete. The sequence repetition time (TR) is then the cardiac R—R interval time.

In gated spin echo, data for each slice location is acquired at a fixed delay from the cardiac R-wave. With variations in the cardiac rhythm, the heart may be at a different phase of the cardiac cycle when data is acquired even though the cardiac delay time may be the same. Normal variations of the cardiac cycle usually result in disproportionately larger changes in the diastolic portion of the cardiac cycle, and gated spin echo images acquired at the end of the cardiac cycle often exhibit blurring or ghosting artifacts.

Another disadvantage of gated spin echo is that images at different slice locations are acquired at different cardiac phases. Hence, it may be difficult to relate information from one spatial location to the next as the heart is pictured at different phases of the cardiac cycle. Furthermore, small structures may also be missed due to inadequate temporal and spatial coverage. Motion of the heart during the cardiac cycle can also lead to image contrast variations from slice to slice due to differential saturation or inter-slice cross-talk.

A short TR gated gradient echo pulse sequence may be used to acquire (CINE) images at multiple time frames of the cardiac cycle. As described in U.S. Pat. No. 4,710,717, conventional CINE pulse sequences run asynchronously to the cardiac cycle with the phase encoding value stepped to a new value at each R-wave trigger. In CINE, each rf excitation pulse is applied at the same spatial location and repeated at intervals of TR in the cardiac cycle. Since the sequence runs asynchronously, the rf excitation pulses may occur at varying time delays from the R-wave from one cardiac cycle to the next. On detection of the next cardiac R-wave, the acquired data from the previous R—R interval are resorted and interpolated into evenly distributed time frames within the cardiac cycle. This method of gating is also known as retrospective gating as the data for the previous R—R interval is resorted only after the current R-wave trigger is detected.

The cardiac cycle is divided into equal time points or frames at which images of the heart are to be reconstructed. In order to reconstruct images at each of these time points, data acquired asynchronously is linearly interpolated to the pre-determined time points in the cardiac cycle. In order to account for variations in the cardiac R—R interval during the scan (from changing heart rate), the interpolation varies from cardiac cycle to cardiac cycle, depending on the R—R interval time. This method allows reconstruction of images at any phase of the cardiac cycle, independent of variations in heart rate. As in gated spin echo, only one k-space phase encoding view is acquired per heart beat. The total image acquisition time is then on the order of 128 heart beats.

Faster scan times can be achieved by segmenting k-space and acquiring multiple phase encoding k-space views per R—R interval. The scan time is speeded up by a factor equal to that of the number of k-space views acquired per image per R—R interval. In this manner, a typical CINE acquisition with a matrix size of 128 pixels in the phase encoding direction can be completed in as little as 16 heart beats, when 8 k-space views per segment are acquired.

Multiple phases of the cardiac cycle can be visualized by repeated acquisition of the same k-space segment within each R—R interval but assigning the data acquired at different time points in the cardiac cycle to different cardiac phases. Thus, the cardiac cycle is sampled with a temporal resolution equal to the time needed to acquire data for a single segment, such that temporal resolution=$vps \times TR$, where vps is the number of k-space lines per segment, the TR is the pulse sequence repetition time. The total scan time is then $$\text{Scan time} = \frac{yres}{vps} \times R - R \text{ time}$$

where yres is the number of phase encoding views in the image. Typically, an image utilizes 128 or more phase encoding views, and 8 views per segment is also often used.

In segmented k-space scans, the total scan time can be substantially reduced by increasing the number of views per segment (vps). However, this is at the expense of reducing the image temporal resolution. As described in U.S. Pat. No. 5,377,680 the image temporal resolution can be increased by sharing views between adjacent time segments to generate images averaged over different time points. The true image temporal resolution is unchanged but the effective temporal resolution is now doubled. View sharing can thus increase the number of cardiac phase images reconstructed without affecting the manner in which the k-space data is acquired.

Prospectively gated, segmented k-space sequences have become popular for cardiac imaging mainly because images can be obtained in a breath-hold and therefore do not suffer from respiratory artifact. Images are formed by acquiring data over a series of heartbeats with data acquisition gated to the QRS complex of the ECG. For images to reconstruct properly, using current methods, the duration of image acquisition must be less than or equal to the duration of the shortest expected R—R interval. In practice, this usually means that the last 10–20% of diastole (~100–200 msec for a heart rate of 60 bpm) is not acquired.

Another problem with many current cardiac-gated sequences is that they sort data based on the time elapsed since the QRS complex. As described in U.S. Pat. No. 4,710,787, this strategy assumes that cardiac phase is directly proportional to time. However, in practice the relationship between cardiac phase and the time elapsed since the QRS is not strictly linear. For example, consider sinus arrhythmia where there is a normal, physiologic change in heart rate that accompanies respiration. The time between the QRS complex and end-diastole is longer for those heart beats with longer R—R intervals and in this case, end-diastole is better defined relative to the following (rather than the preceding) QRS complex. This can be seen readily in the normal ECG where the P wave (which signifies atrial contraction) is better correlated temporally to the following (rather than the preceding) QRS complex. This variation in the R—R interval and the fact that a specific cardiac phase occurs at a different delay time from the R-wave with this variation, leads to image blurring in fast segmented k-space pulse sequences and also in conventional CINE pulse sequences.

SUMMARY OF THE INVENTION

The present invention is a method for prospectively gating and retrospectively sorting MR imaging data acquired during successive cardiac cycles. More specifically, a cardiac gating signal is produced and time-stamped MR data is continuously acquired during successive cardiac cycles. A cardiac cycle systolic period and a cardiac cycle diastolic period are determined for each cardiac cycle and the time stamp associated with the acquired MR data is correlated with a systolic cardiac phase or a diastolic cardiac phase. Images are reconstructed at specified cardiac phases using MR image data which is acquired during successive cardiac cycles and which is selected on the basis of its correlated cardiac phase.

A general object of the invention is to reduce image blurring in fast segmented k-space and CINE acquisitions. Based on the length of the R—R interval, the systolic and diastolic periods within the interval are determined. The time stamped MR data may then be correlated with a phase of the systolic period or a phase of the diastolic period rather than a phase of the entire R—R interval. A data set from which a more accurate image may be reconstructed is thus formed by collecting MR data acquired at the same systolic phase or the same diastolic phase.

Another object of the invention is to more efficiently acquire MR data during a fast cardiac MRI scan. Data is acquired throughout each cardiac cycle regardless of the R—R interval. All of this data can be accurately correlated with a systolic or diastolic phase and used to reconstruct images at selected cardiac phases.

GENERAL DESCRIPTION OF THE INVENTION

Figure 2:
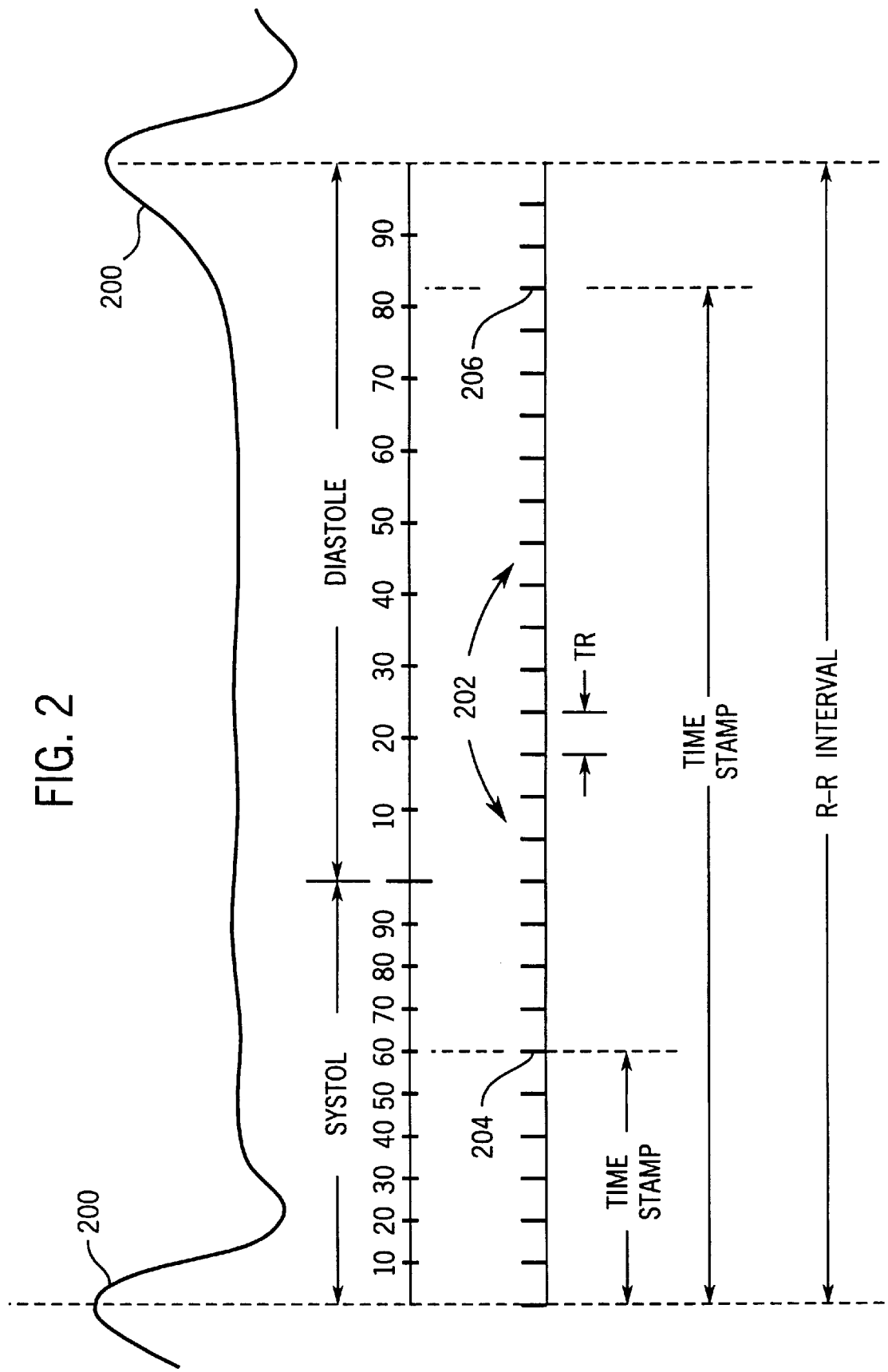
FIG. 2 is a graphic representation of the acquisition of MR data during successive cardiac cycles using the MRI system of FIG. 1.

To practice the present invention NMR data is acquired throughout each cardiac cycle. As shown in FIG. 2, the k-space views for each segment 202 are repeatedly acquired until the next QRS cardiac trigger signal 200 is received. Because the R—R interval may vary from one cardiac cycle to the next, this means that the amount of acquired data will also vary.

Regardless of the R—R interval, the heart cycles completely through a systolic period and a diastolic period, and therefore, acquired data is available to depict the heart at any phase of its cycle. An objective of this present invention is to correlate the acquired NMR data with the particular cardiac phase, or phases to be imaged.

During the scan each acquired k-space view is time-stamped with respect to the QRS trigger 200. More specifically, its time of acquisition is equal to the repetition time (TR) of the pulse sequence times the number of views acquired since the last QRS trigger.

To deal with the variations in R—R interval during the scan, the time-stamped views are correlated with the systolic period or the diastolic period of the cardiac cycle. The systolic and diastolic periods are calculated using a model of the cardiac cycle in which:

systolic period=546 ms−2.1 (60000)/$R$-$R$ interval; and diastolic period=$R$-$R$ interval−systolic period.

Each time-stamped view was acquired at some point in either the systolic or diastolic period, and its acquisition time can be correlated with a percentage of the systolic period or a percentage of the diastolic period. As shown in FIG. 2, for example, the view acquired at 204 correlates with 60% systole and the view acquired at 206 correlates with 80% diastole.

To reconstruct an image at a particular cardiac phase, the corresponding views in each cardiac cycle are used. In other words, if an image depicting the heart at 50% through the systolic period is reconstructed, the views in each cardiac cycle which correlate with 50% systole are used. Typically, the views will not correlate exactly with the desired cardiac phase, and interpolation is employed to calculate the exact value. For example, one view may correlate to 47% systolic phase and the next view may correlate to 52% systolic phase. The 50% systolic view is then calculated by linearly interpolating between these two views. For segmented k-space scans in which several different k-space views are acquired repeatedly during an R—R interval, the interpolation is performed to generate the different k-space views for that segment at the requisite cardiac phase. For example, with 4 views per segment, views k1, k2, k3, k4 are encoded per segment. If the first 4 k-space views are acquired at times corresponding to 46%, 47%, 48%, 49% of the systolic phase, and the next 4 k-space views correspond to 50%, 51%, 52%, 53% of the systolic phase, all 4 views are interpolated to the 50% systolic phase point from the two adjacent data segments.

DESCRIPTION OF THE PREFERRED EMBODIMENT

Figure 1:
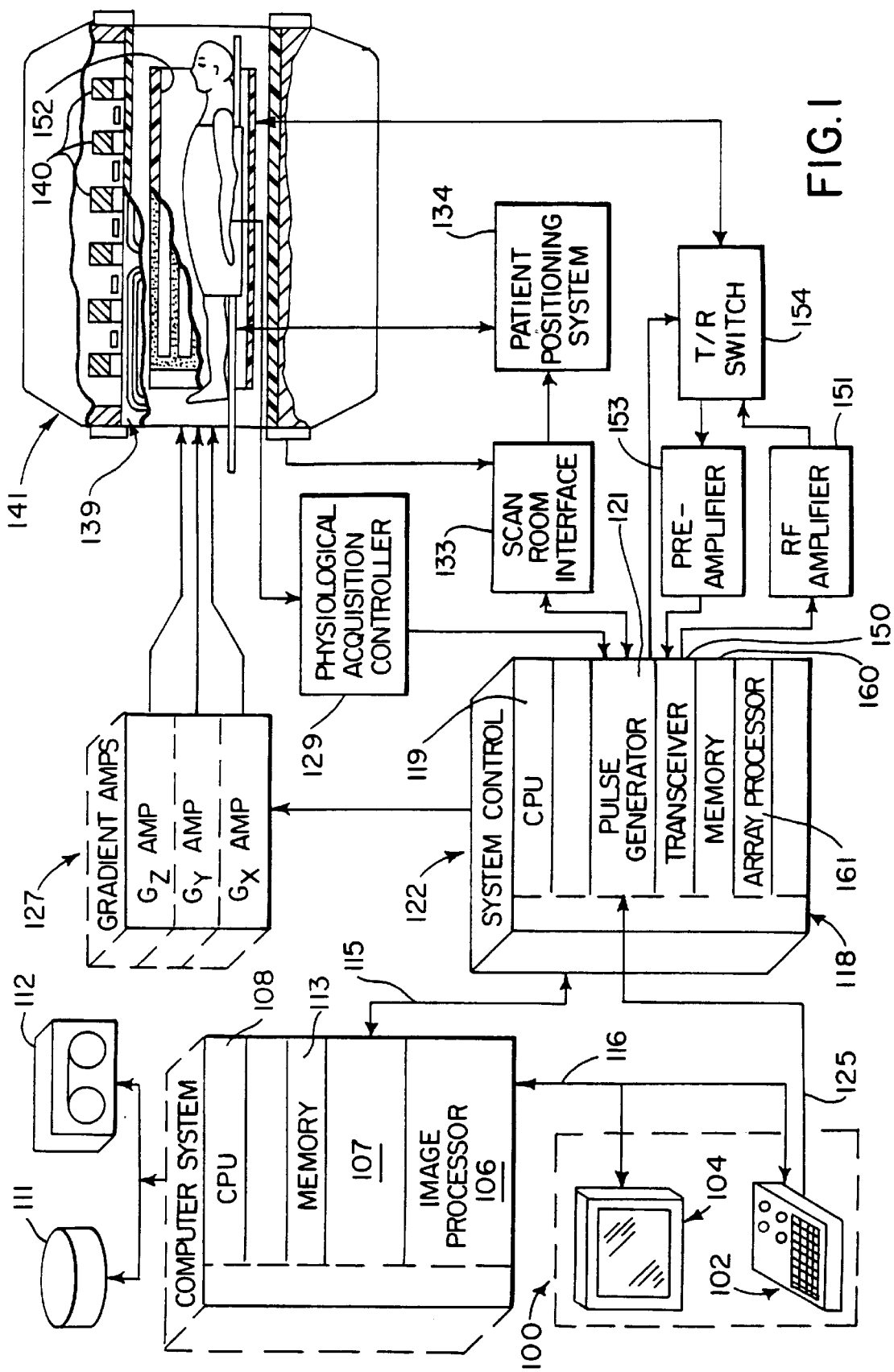
FIG. 1 is a block diagram of an MRI system which employs the present invention.

Referring to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes attached to the patient. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a surface coil) to be used in either the transmit or receive mode.

The NMR signals picked up by the RF coil 152 are digitized by the transceiver module 150 and transferred to a memory module 160 in the system control 122. When the scan is completed and an array of raw k-space data has been acquired in the memory module 160. As will be described in more detail below, this raw k-space data is rearranged into separate k-space data arrays for each cardiac phase image to be reconstructed, and each of these is input to an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104. For a more detailed description of the transceiver 150, reference is made to U.S. Pat. Nos. 4,952,877 and 4,992,736 which are incorporated herein by reference.

Referring particularly to FIG. 2, the cardiac acquisition in accordance with the preferred embodiment employs a series of fast gradient echo pulse sequences, with the repetition time, TR, of each gradient echo pulse sequence of between 6 and 15 ms, depending on the type of gradient hardware available and imaging parameters chosen. These pulse sequences are executed during the interval between the cardiac trigger signals 200 referred to as the R—R interval. The length of the R—R interval is a function of the patient's heart rate.

In a fast cardiac acquisition using gradient echoes, the R—R interval is divided up into many short acquisitions, with each acquisition being a fast gradient acquisition pulse sequence with a nominal flip angle of between 20–30°. Each fast gradient echo acquisition acquires an NMR signal representing a single line of k-space which is referred to herein as a view. Adjacent fast gradient echo acquisitions may be further combined into segments 202 where the data from each segment includes a plurality of different views. In the preferred embodiment, each segment 202 contains 8 views and k-space is traversed in a sequential strip fashion during the scan. That is, views −60 through −53 are acquired on the first cardiac trigger, views −52 through −45 on the next cardiac trigger, and so forth. The last cardiac trigger picks up views −64 through −61 and views +60 through +63. This view order is preferred as it provides minimal image artifacts and also allows the central 8 low spatial frequency views to be acquired during a single R—R interval so that image artifacts resulting from inconsistencies between cardiac triggers are minimized. Another advantage of this sequential strip view order is that views may be shared between groups with minimal image artifacts. However, depending on the particular application, any other appropriate view acquisition order can also be used.

Figure 3:
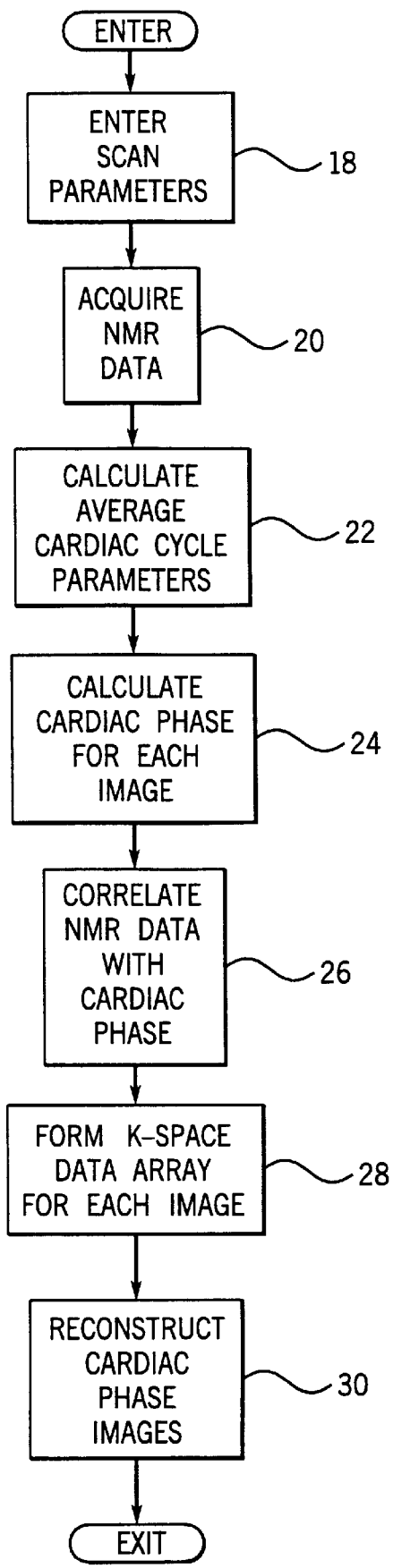
FIG. 3 is a flow chart of the steps performed by the MRI system of FIG. 1 to practice the preferred embodiment of the invention.

The method of the present invention is implemented in the MRI system of FIG. 1 under the direction of a program indicated by the flow chart in FIG. 3. Prior to the scan the operator enters the number of cardiac phases to be imaged, along with the other scan parameters as indicated at process block 18. The scan is performed, as indicated at process block 20, by acquiring k-space views for successive segments until all the k-space phase encoding views are acquired. One segment is repeated throughout a complete cardiac cycle so that k-space data for the views in the segment is acquired throughout the systolic and diastolic periods. The acquired data is stored separately for each heart beat in the order in which it is acquired, such that it is effectively time stamped. In other words, the time during the cardiac cycle at which a view is acquired is indicated by its location in the raw data array and this time may be calculated by multiplying the pulse sequence repetition time (TR) by the number of views acquired since the last trigger signal 200. Similarly, the duration of each corresponding R—R interval during the scan is also recorded.

Images are reconstructed so that the prescribed number of cardiac phase images are uniformly spaced in time over an average cardiac cycle R—R interval. First, an average cardiac cycle is defined at process block 22 by calculating an average R—R interval as follows:

$RR_{AVG}$=TR (total views acquired)/(total heart beats).

The cardiac phase images are distributed uniformly over this average R—R interval. These uniformly spaced times are then converted to a cardiac phase which is expressed as a percentage of an average systole period or an average diastole period. The average systolic and diastolic periods for males and females are calculated at process block 22 based on a model of the cardiac cycle:

$$\text{systolic}_{AVG} = 549 \text{ ms} - 2.1 \ (HR)$$

$$\text{diastolic}_{AVG} = RR_{AVG} - \text{systolic}_{AVG},$$

where HR is the average heart rate in beats per minute calculated as follows:

$$HR = (60000)/RR_{AVG}$$

To reconstruct 20 uniformly spaced image for a patient with an $RR_{AVG}$ of 1 sec., for example, one calculates a HR of 60 pbm, an average systolic period of 420 ms, and an average diastolic period of 580 msec. The images are evenly spaced in time throughout the cardiac cycle at 50 msec intervals (i.e., 1 sec/20). These 50 msec time points are converted into cardiac phases at process block 24. In the above example, therefore, the phase 0 image occurs at 0/420=0% through systole, the phase 1 image occurs at 50/420=12% through systole, . . . the phase 8 image occurs at 400/420=95% through systole, the phase 9 image occurs at 30/580=5% through diastole, . . . and the phase 19 image occurs at 530/580=91% through diastole. Thus, each of the cardiac phase images that are to be reconstructed are correlated with a specific cardiac cycle phase expressed as a portion of the systolic or diastolic period.

The cardiac phase images are reconstructed by selecting the k-space view from each cardiac cycle which corresponds to the cardiac phase of the image. As indicated by process block 26, the first step in the reconstruction process is to correlate the acquired time-stamped NMR data in the raw data array to cardiac phase. This is accomplished as follows:

If the average RR interval is 1000 ms (corresponding to a heart rate of 60 bpm), and 10 phases are reconstructed,

| | | |
|---|---|---|
| $RR_{avg}$ | = | 1000 ms |
| $\Delta t$ | = | 100 ms |
| Time to 9th phase | = | 900 ms |
| systolic$_{avg}$ | = | 420 ms |
| diastolic$_{avg}$ | = | 580 ms |

The second phase then corresponds to 83% of the systolic period. If on the nth R—R interval, the RR interval is decreased to 833 ms (heart rate increased to 72 bmp) the systolic period for that RR interval is

| | | |
|---|---|---|
| systolic$_n$ | = | 546 − 2.1 × 72 |
| | = | 395 ms |
| diastolic$_n$ | = | 438 ms |

The 83% diastolic point then corresponds to a delay of 758 ms for the nth RR interval. Either the closest views to that time point are used or the data for the closest views are interpolated to that time point corresponding to the 9th cardiac phase. For the other RR interval where the RR interval time is different, the 83% diastolic period occurs at a different delay from the R-wave and different views are utilized for the interpolation, depending on their proximity to the 83% diastolic period point. Thus, data for each cardiac phase is interpolated from the recorded data according to the time stamp for each view and the RR interval period in which they were acquired.

As indicated at process block 28, a complete k-space data array is then formed by selecting the appropriate k-space views from the raw data array. The calculated cardiac phase for the image is used to make this selection, and those k-space views with the same cardiac phase are selected from the raw data array to form the k-space data array. In most instances an exact cardiac phase match will not be available and a k-space view may be calculated by linearly interpolating between the two acquired k-space views that straddle the desired cardiac phase.

After the k-space data array has been formed, a cardiac phase image is reconstructed as indicated at process block 30. In the preferred embodiment this is a 2-D Fourier transformation of the k-space data as explained above.

The present invention uses a cardiac model that separately normalizes systole and diastole as described by Mirsky I. Ghista, DN, Sandler H. Cardiac Mechanics: Physiological, Clinical and Mathematical Considerations. John Wiley and Sons, Inc., New York, 1974. p. 237. This is a more accurate reflection of what occurs physiologically than uniformly normalizing the entire R—R interval, since changes in heart rate disproportionally affect the duration of diastole compared to systole. The model for describing the duration of diastolic and systolic intervals based on heart rate was determined empirically after studying normal men and women at rest. The numerical formula is a good predictor of the systolic duration on an individual basis with a standard deviation of ±14 ms. This corresponds to only a ±3% error for a typical individual with a heart rate of 60 bpm and a systolic duration of 420 msec.

The accuracy of the model is also surprisingly good even in many disease states. In a series of twenty-seven patients with congestive heart failure the standard deviation between the predicted and measured systolic interval was only ±20 ms. Additional data suggest that this formula may provide a reasonable approximation even for patients with known cardiac pathology such as ischemic heart disease, cardiomyopathy, and valvular insufficiency and stenosis. Adrenergic stimulation has been noted to result in a shorter than predicted systolic duration, however the maximum deviation from the predicted value is still only about 10%. It is not known to what extent the model used will be accurate for patients undergoing a pharmacological stress test during MR imaging. However, if additional accuracy is desired, data can be collected to determine a numerical formula for any specific physiologic state and this formula can be substituted in the calculations described above.

Figure 4:
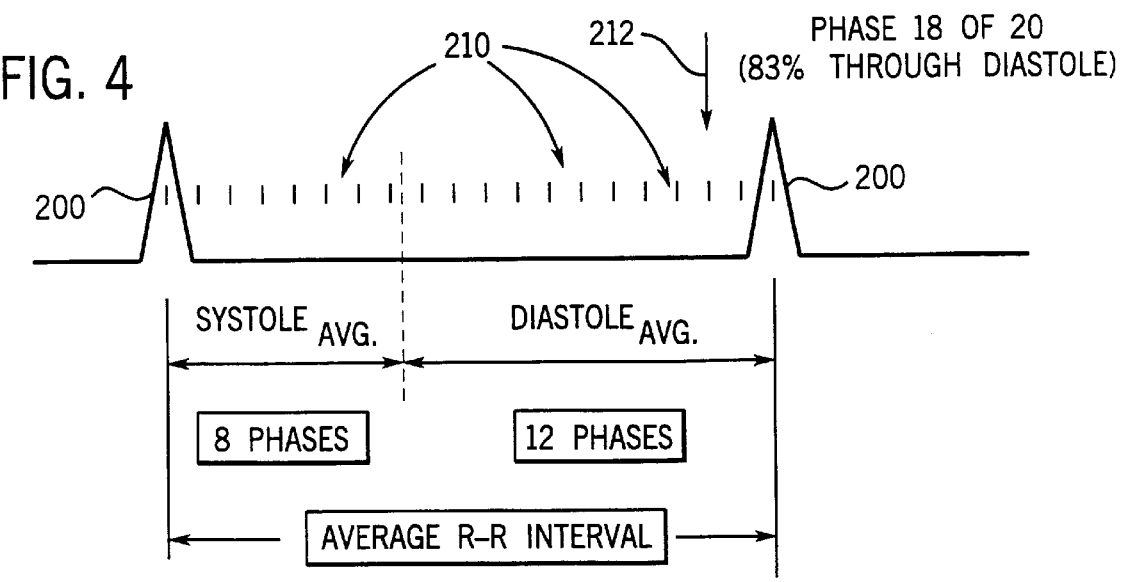
FIGS. 4–6 are graphic illustrations of cardiac cycles that occur during a typical scan in which the present invention is used.
Figure 5:
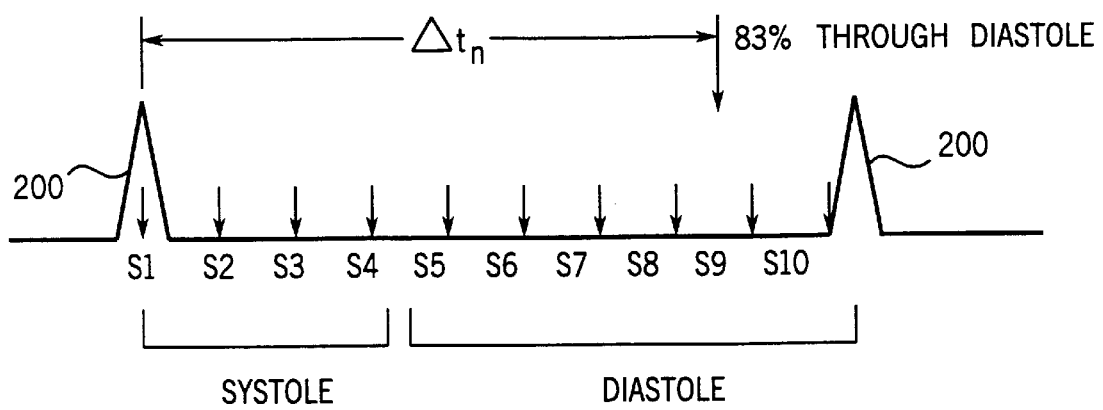
Figure 6:
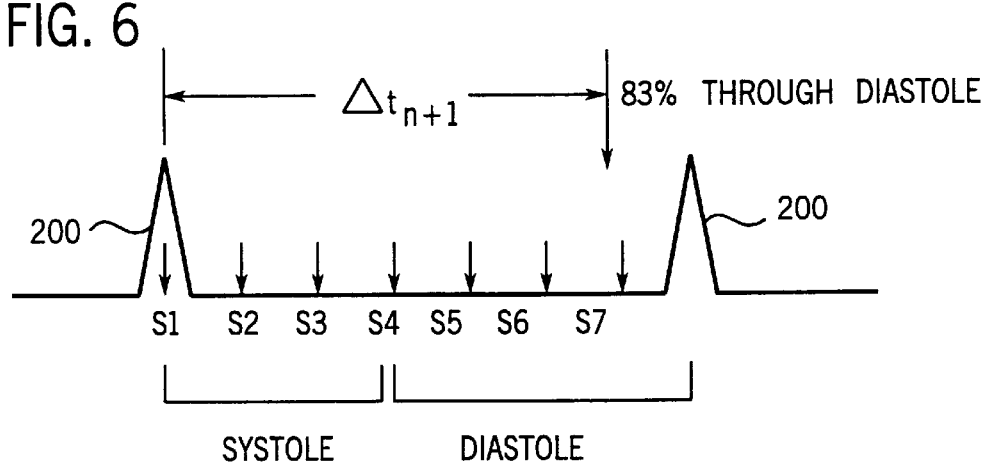

The operation of the present invention is shown graphically in FIGS. 4–6. FIG. 4 shows an average R—R interval which is calculated after a scan has been performed. The average systolic and diastolic periods are also calculated and the 20 prescribed cardiac phase images to be produced are shown uniformly distributed throughout the R—R interval. The 18th cardiac phase image, for example, occurs at 83% through the average diastolic period as shown by the arrow 212.

FIG. 5 depicts an exemplary "nth" R—R interval during the scan which is longer than the average R—R interval of FIG. 4. The location of 83% diastolic phase corresponds to a time delay of $\Delta t_n$ which occurs between the segments S9 and S10.

FIG. 6 depicts an exemplary "n+1$^{th}$" R—R interval during the scan which is shorter than the average R—R interval of FIG. 4. The location of the 83% diastolic phase corresponds to a time delay of $\Delta t_{n+1}$ which occurs between the segments S6 and S7. Notice that the diastolic period varies more than the systolic period in these exemplary R—R intervals.

We claim:

1. A method for producing an NMR image depicting the heart of a subject at a selected cardiac phase, the steps comprising:
    a) producing a signal indicative of successive cycles of the subject's heart;
    b) acquiring NMR data views throughout each of said successive cycles, each NMR data view being associated with a time stamp which indicates when the view was acquired within one of said heart cycles;
    c) calculating an average heart cycle by averaging intervals between the signals indicative of successive cycles of the subject's heart;
    d) forming an array of NMR data from which an image depicting the heart at the selected cardiac phase can be reconstructed by:
        i) correlating the selected cardiac phase with a desired point neither a systolic period or a diastolic period of the heart cycle in which the NMR data was acquired; and
    e) reconstructing an image from the array of NMR data formed from the selected acquired NMR data.

2. The method as recited in claim 1 in which the systolic period and the diastolic period of the average heart cycle are calculated based on a model of the heart.

3. The method as recited in claim 1 in which the systolic period is calculated as follows:

systolic period=546−2.1(60,000)/R—R, where R—R is the averaged intervals.

4. A method for producing an NMR image depicting the heart of a subject at a selected cardiac phase, the steps comprising:
    a) producing a signal indicative of successive cycles of the subject's heart;
    b) acquiring NMR data views throughout each of said successive cycles, each NMR data view being associated with a time stamp which indicates when the view was acquired within one of said heart cycles;
    c) forming an array of NMR data from which an image depicting the heart at the selected cardiac phase can be reconstructed by:
        i) correlating the selected cardiac phase with a desired point in either a systolic period or a diastolic period of an average heart cycle;
        ii) selecting acquired NMR data which correlates with the desired point in either the systolic period or diastolic period of the heart cycle in which the NMR data was acquired by:
            calculating the systolic period and diastolic period of the heart cycle in which the NMR data was acquired; and
            determining the time stamp of NMR data acquired during said heart cycle which corresponds to said desired point in either the calculated systolic or diastolic period; and
    d) reconstructing an image from the array of NMR data formed from the selected acquired NMR data.

5. The method as recited in claim 4 in which NMR data selected in step c) ii) is calculated by interpolating between NMR data views with associated time stamps adjacent said determined time stamp.

6. An MRI system for producing an NMR image depicting the heart of a subject at a selected cardiac phase, the combination comprising:
    means for producing a cardiac signal which indicates the beginning of successive cycles of the subject's heart;
    a pulse generator for directing the MRI system to perform a series of NMR imaging pulse sequences to acquire NMR data views substantially throughout each of a succession of said heart cycles;
    means for storing the acquired NMR data views;
    means for calculating an array of NMR data from which an image depicting the patient's heart at a selected cardiac phase can be reconstructed, said means for calculating including:
        a) means for calculating the systolic period and diastolic period ineach of the successive heart cycles;
        b) means for correlating the selected cardiac phase with a point in either a systolic period or a diastolic period of a heart cycle; and
        c) means for selecting NMR data views from the means for storing which were acquired at said point in either the systolic period or diastolic period in said succession of heart cycles; and
    means for reconstructing an image from the selected array of NMR data views.

7. The MRI system as recited in claim 6 in which the means for correlating the selected phase includes means for calculating an average heart cycle from the succession of heart cycles.

8. The MRI system as recited in claim 6 in which the means for selecting NMR data views includes means for interpolating between stored NMR data views.

* * * * *

UNITED STATES PATENT AND TRADEMARK OFFICE
CERTIFICATE OF CORRECTION

PATENT NO. : 5,997,883
DATED : December 7, 1999
INVENTOR(S) : Frederick H. Epstein, et al.

It is certified that error appears in the above-identified patent and that said Letters Patent is hereby corrected as shown below:

Claim 1, Col.9, line 50, "neither" should be --in either--.

Signed and Sealed this

Twenty-fourth Day of April, 2001

Attest:

NICHOLAS P. GODICI

*Attesting Officer*    *Acting Director of the United States Patent and Trademark Office*